United States Patent
Thabuis et al.

(10) Patent No.: US 10,273,499 B2
(45) Date of Patent: Apr. 30, 2019

(54) R-GENES IN COUPLING PHASE

(71) Applicant: RIJK ZWAAN ZAADTEELT EN ZAADHANDEL B.V., De Lier (NL)

(72) Inventors: Arnaud Paul Pierre Thabuis, Montfavet (FR); Johannes Wilhelmus Schut, Wouw (NL); Arie Vogelaar, Dordrecht (NL)

(73) Assignee: RIJK ZWAAN ZAADTEELT EN ZAADHANDEL B.V., de Lier (NL)

( * ) Notice: Subject to any disclaimer, the term of this patent is extended or adjusted under 35 U.S.C. 154(b) by 1342 days.

(21) Appl. No.: 13/785,126

(22) Filed: Mar. 5, 2013

(65) Prior Publication Data

US 2013/0269066 A1 Oct. 10, 2013

Related U.S. Application Data

(63) Continuation-in-part of application No. PCT/EP2013/053367, filed on Feb. 20, 2013.

(30) Foreign Application Priority Data

Feb. 20, 2012 (EP) .................................. 12156259

(51) Int. Cl.
- *C12N 15/82* (2006.01)
- *A01H 5/00* (2018.01)
- *A01H 5/12* (2018.01)
- *A01H 1/04* (2006.01)

(52) U.S. Cl.
CPC ........... *C12N 15/8282* (2013.01); *A01H 1/04* (2013.01); *A01H 5/00* (2013.01); *A01H 5/12* (2013.01)

(58) Field of Classification Search
None
See application file for complete search history.

(56) References Cited

U.S. PATENT DOCUMENTS

| | | |
|---|---|---|
| 5,684,226 A | 11/1997 | Sarreal |
| 5,973,232 A | 10/1999 | Waycott et al. |
| 2010/0229255 A1 | 9/2010 | Moor et al. |

OTHER PUBLICATIONS

International Union for the Protection of New Varieties of Plants, TG/13/10, (Apr. 6, 2011).*
Crute, 1992, Euphytica 63: 95-102.*
Witsenboer et al., 1997, Genome 40: 923-936.*
International Preliminary Report on Patentability and Written Opinion of the International Searching Authority dated Aug. 26, 2014, which issued during prosecution of International Application No. PCT/EP2013/053367.
International Search Report dated Jun. 17, 2013, which issued during prosecution of International Application No. PCT/EP2013/053367.
Crute, "The role of resistance breeding in the intergrated control of downy mildew (*Bremia lactucae*) in protected lettuce" Euphytica 63(1-2):95-102, Jan. 1992.
Farrara, et al. "Genetic analysis of factors for resistance to downy mildew (*Bremia lactucae*) in species of lettuce (*Lactuca sativa* and *L. serriola*)" Plant Pathology 36(4):499-514, Dec. 1987.
Maisonneuve, et al. "Rapid mapping of two genes for resistance to downy mildew from Lactuca serriola to existing clusters of resistance genes" Theoretical and Applied Genetics 89(1):96-104, Jan. 1994.
Oertel, "Lettuce: Guidelines for the conduct of Tests for Distinctness, Uniformity and Stability" The International Union for the Protection of New Varieties of Plants (UPOV), Apr. 2006.
Wroblewski, et al. "Silencing of the major family of NBS-LRR-encoding genes in lettuce results in the loss of multiple resistance specificities" The Plant Journal 51(5):803-818, Sep. 2007.

* cited by examiner

*Primary Examiner* — Bratislav Stankovic
(74) *Attorney, Agent, or Firm* — Duane Morris LLP; Thomas J. Kowalski; Deborah L. Lu

(57) ABSTRACT

The invention relates to plants and plant parts, in particular lettuce plants (*Lactuca sativa* L.), which are resistant to *Bremia lactucae*. The invention also relates to seeds of these plants capable of producing *Bremia lactucae* resistant plants. The invention further relates to methods for obtaining said plants with altered genotypes and seeds thereof, which are resistant to *Bremia lactucae*.

10 Claims, 2 Drawing Sheets

Specification includes a Sequence Listing.

Fig. 1

Heterozygous in coupling phase:

F1

| Dm3 Dm6 R18 | dm3 dm6 r18 | X | Dm3 Dm6 R18 | dm3 dm6 r18 |

F2    1    :    2    :    1

| Dm3 Dm6 R18 | Dm3 Dm6 R18 | | Dm3 Dm6 R18 | dm3 dm6 r18 | | dm3 dm6 r18 | dm3 dm6 r18 | susceptible to all *Bremia* races that would be covered by Dm3, Dm6 and R18

R-GENES IN COUPLING PHASE

RELATED APPLICATIONS AND INCORPORATION BY REFERENCE

This application is a continuation-in-part application of international patent application Serial No. PCT/EP2013/053367 filed 20 Feb. 2013, which claims benefit of European patent application Serial No. 12156259.9 filed 20 Feb. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to plants and plant parts, in particular lettuce plants (*Lactuca sativa* L.), which are resistant to *Bremia lactucae*. The invention also relates to seeds of these plants capable of producing *Bremia lactucae* resistant plants. The invention further relates to methods for obtaining said plants with altered genotypes and seeds thereof, which are resistant to *Bremia lactucae*.

BACKGROUND OF THE INVENTION

Downy mildew is a serious pest worldwide, in both glasshouse and open field production of lettuce plants (*Lactuca sativa* L.). Lettuce downy mildew is caused by the fungus *Bremia lactucae*, belonging to a class of relatively primitive fungi known as Oomycetes. The fungus is an obligate parasite capable of infecting a lettuce plant in any growth stage from seedling to mature plant.

Co-evolution of the plant and the pathogen has led to an arms race in which the resistance of the plant can be broken down as a consequence of the capability of the pathogen to interact with and modify alternative host targets or the same targets in a different way.

One breeding technique to slow down the fast gain of virulence from *Bremia* population is to associate different *Bremia* resistance genes (also called pyramiding or stacking). One limit of this strategy is that the different *Bremia* resistance genes (R-genes) are grouped in a limited number of locations. Such locations are called resistance gene clusters, In lettuce, at least 4 major resistance gene clusters are known lying on chromosome 1, chromosome 2, chromosome 4, and chromosome 8, respectively. R-genes from the same cluster can segregate as alleles or tightly linked genes. Therefore, it is often impossible to stack R-genes from the same cluster, because genes on the same cluster are in repulsion phase with each other, and are inherited like alternative alleles of the same locus. In breeding lettuce, which is a diploid crop, the opportunity of pyramiding dominant *Bremia*-genes on the same resistance gene cluster is therefore limited to a maximum of two genes per cluster. This maximum can only be reached in heterozygous plants with a single copy for each gene. However, providing heterozygous lettuce plants to growers implies the use of hybrid varieties, Unfortunately the production of hybrid lettuce seed is considered too expensive, too risky and too complicated. Therefore in practice almost all lettuce varieties are inbred lines. In an inbred line the number of genes per cluster is limited to one, which is then present in a homozygous state with two copies for the gene.

As mentioned earlier, there is a continuous arms race going on between the plant and the pathogen and during this race R-genes are constantly broken and breeders need alternative resistance sources in order to keep producing resistant varieties. Every new combination of R-genes is therefore a valuable asset for the breeder.

Citation or identification of any document in this application is not an admission that such document is available as prior art to the present invention.

SUMMARY OF THE INVENTION

Given the significant advantages of stacking R-genes, it is the Object of the present invention to provide lettuce plants with a new combination of R-genes in coupling phase, which were previously only found in repulsion phase, inherited as alternative alleles, and therefore not stackable.

In the research leading to the present invention new lettuce plants were developed which have in their genome *Bremia* R-genes Dm3, Dm6 and R18 in coupling phase. These three R-genes are all on the resistance cluster of chromosome 2 of *Lactuca sativa* L. Together these genes confer resistance to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

Although a similar resistance profile may be obtained by combining other R-genes, the advantage of having these three genes in coupling phase is the fact that the possibilities of one resistance gene cluster are used more extensively and that the breeder has new stacking possibilities at hand, slowing down the virulence of the pathogen.

The invention thus relates to a lettuce plant resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, which plant may comprise a genetic determinant which causes the resistance and which genetic determinant is obtainable by introgression from a plant grown from seeds of which a representative sample was deposited under accession number NCIMB 41761, and wherein the said genetic determinant in the seeds of seed deposit number NCIMG 41761 is at least linked to marker SCM05 with SEQ ID NO:4, marker LR0029 with SEQ ID NO:5, and marker LK0036 with SEQ ID NO:6, and optionally also to one or more of the markers selected from the group consisting of marker SCW09 with SEQ ID NO: 1, marker CL922 with SEQ ID NO:2, marker SCV12 with SEQ ID NO:3, marker LR0096 with SEQ ID NO:7, and marker SCI11 with SEQ ID NO:8.

The invention also relates to a lettuce plant resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, wherein said resistance is conferred by a genetic determinant, characterized in that said genetic determinant consists of *Bremia* R-genes Dm3, Dm6 and R18 in coupling phase, and wherein said genetic determinant is obtainable from a plant grown from seeds of which a representative sample was deposited under accession number NCIMB 41761.

The invention further may comprise a lettuce plant resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, wherein said resistance is conferred by a genetic determinant, characterized in that said genetic determinant consists of *Bremia* R-genes Dm3, Dm6 and R18 in coupling phase, and wherein said genetic determinant in plants grown from seeds deposited under accession number NCIMB 41761 is identifiable by the presence of marker SCM05 with SEQ ID NO:4, marker LR0029 with SEQ ID NO:5, and marker LK0036 with SEQ ID NO:6, and optionally also markers selected from the group consisting of marker SCW09 with SEQ ID NO:1, marker CL922 with SEQ ID NO:2, marker SCV12 with SEQ ID NO:3, marker LR0096 with SEQ ID NO:7, and marker SCI11 with SEQ ID NO:8. In a particular embodiment, the genetic determinant may comprise genes Dm3, Dm6 and R18 in coupling phase. The present invention thus provides a new and unique combination of R-genes, giving the breeders a new alternative for developing *Bremia lactucae* resistant lettuce varieties.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "may comprise", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposit

Seeds comprising the R-genes Dm3, Dm6 and R18 in coupling phase were deposited under NCIMB deposit accession number NCIMB 41761 on 29 Sep. 2010 with NCIMB Ltd., Ferguson Building, Craibstone Estate, Bucksburn, Aberdeen, AB21 9YA Scotland, UK.

The Deposit with NCIMB, under deposit accession number 41761 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 depicts selfing a heterozygous F1 population in coupling phase.

DETAILED DESCRIPTION OF THE INVENTION

Figure 2:
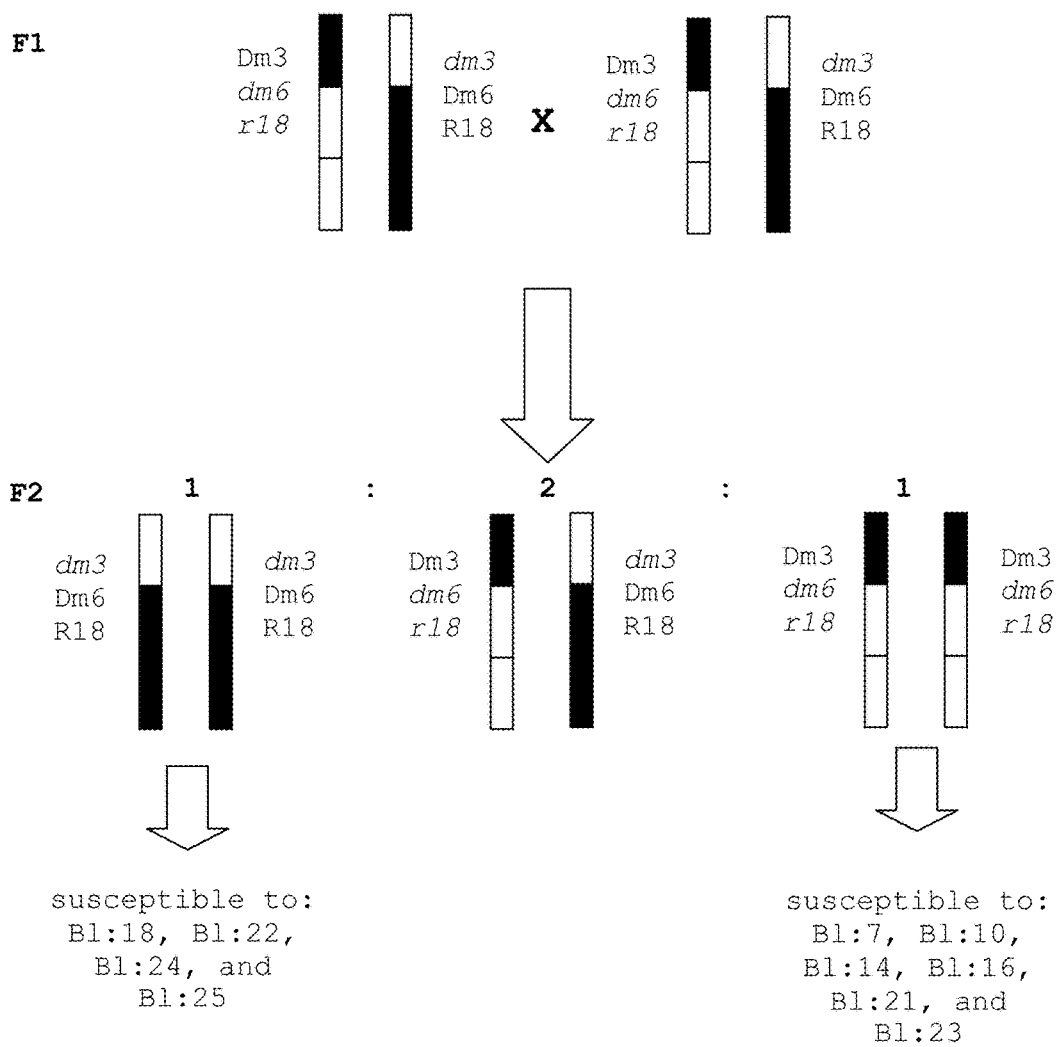
FIG. 2 depicts selfing a heterozygous F1 population in repulsion phase.

The present invention thus provides lettuce plants, which are resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, wherein said resistance is conferred by R-genes Dm3, Dm6 and R18, which are present in coupling phase on a genetic determinant, which is as found in plants grown from seeds of which a representative sample was deposited under NCIMB deposit accession number NCIMB 41761 on 29 Sep. 2010.

The combination of these R-genes from the same cluster, such that they are in coupling phase instead of repulsion phase, offers many advantages. The R-genes in coupling phase may be regarded as a new super R-gene which would confer resistance against more *Bremia lactucae* races. Also, the inheritance of R-genes in coupling phase is similar to that of a single gene and therefore increases breeding efficiency.

The invention thus relates to a lettuce plant having the three R-genes Dm3, Dm6 and R18, present in its genome in coupling phase, such that the three R-genes are inherited together in a dominant fashion as a single allele.

In one embodiment the lettuce plant of the invention carries the R-genes Dm3, Dm6 and R18 as a single allele as present in the genome of seeds of which a representative sample was deposited under accession number NCIMB 41761, which allele causes resistance to at least *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

According to a further aspect thereof, the invention provides a genetic determinant which may comprise the R-genes Dm3, Dm6 and R18, characterised in that said R-genes are in coupling phase and thus behave as one allele of a single dominant gene. Resistances against *Bremia* races covered by the separate R-genes Dm3, Dm6 and R18 and those R-genes in coupling phase are specified in Table 1. Resistances against six *Bremia* races are conferred by more than one R-gene, resistances against the remaining *Bremia* races are conferred by only one R-gene. The Dm3 specific resistances are against *Bremia* races B1:18, B1:22, B1:24, B1:25 and B1:28. The only Dm6 specific resistance is against B1:17. Resistances specifically conferred by R18 are against *Bremia* races B1:2, B1:7, B1:10, B1:14, B1:21, and B1:23 (See Table 1).

TABLE 1

Resistances conferred by R-genes Dm3, Dm6 and R18 separately and in coupling phase

| Bremia lactucae strain | R-gene Dm3 | R-gene Dm6 | R-gene R18 | Dm3 + Dm6 + R18 in coupling phase |
|---|---|---|---|---|
| Bl:1 | − | − | − | − |
| Bl:2 | + | + | (−) | (−) |
| Bl:4 | − | (−) | (−) | − |
| Bl:5 | + | − | − | − |
| Bl:6 | − | (−) | − | − |
| Bl:7 | + | + | −*** | − |
| Bl:10 | + | + | −*** | − |
| Bl:12 | − | + | − | − |
| Bl:13 | + | (−) | − | − |
| Bl:14 | + | + | −*** | − |
| Bl:15 | + | − | − | − |
| Bl:16 | + | + | −*** | − |
| Bl:17 | + | −** | + | − |
| Bl:18 | −* | + | + | − |
| Bl:20 | + | + | + | + |
| Bl:21 | + | + | −*** | − |
| Bl:22 | −* | + | + | − |
| Bl:23 | + | + | −*** | − |
| Bl:24 | −* | + | + | − |
| Bl:25 | −* | + | + | − |
| Bl:26 | + | + | + | + |
| Bl:27 | + | + | + | + |
| Bl:28 | −* | + | + | − |

− indicates a resistant reaction
(−) also indicates a resistant reaction, but in the seedling test a very limited amount of sporulation might be observed
+ indicates a susceptible reaction
*Resistance unique for Dm3
**Resistance unique for Dm6
***Resistance unique for R18

In one embodiment the invention relates to a lettuce plant resistant to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, wherein said resistance is obtainable by introgression from a plant grown from seeds of which a representative sample was deposited with the NCIMB under accession number NCIMB 41761, and wherein the said resistance in the seeds of the seed deposit number NCIMB 41761 is linked to marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

In another embodiment the invention relates to a lettuce plant resistant to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, said plant which may comprise an introgression which may comprise Dm3, Dm6 and R18, wherein said introgression is obtainable from a lettuce plant of which representative seed is deposited with the NCIMB under accession number NCIMB 41761 and wherein the said introgression in the seeds of the seed deposit number NCIMB 41761 is linked to marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

In another embodiment the invention relates to a lettuce plant resistant to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, said plant which may comprise an introgression obtainable from a lettuce plant, representative seeds of which were deposited with the NCIMB under accession number NCIMB 41761, which introgression may comprise genes Dm3, Dm6 and R18 in coupling phase linked to the marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

An introgression in this respect relates to a part of chromosome 2 that may comprise the resistance genes Dm3, Dm6 and R18 in coupling phase.

The markers SCM05, LR0029 and LK0036 together provide a haplotype pattern that is unique for the R-genes Dm3, Dm6 and R18 in coupling phase as found in seeds of the deposit, which were deposited with the NCIMB under accession number NCIMB 41761. The said haplotype is thus predictive for the R-genes Dm3, Dm6 and R18 in coupling phase as found in seeds of the said deposit. The haplotype may be extended with one or more of the markers SCW09, CL922, SCV12, LR0096 and SCI11. Other, more extended haplotypes thus consist for example of markers SCW09, CL922, SCV12, SCM05, LR0029 and LK0036 or markers SCW09, CL922, SCV12, SCM05, LR0029, LK0036, LR0096 and SCI11 or other combinations that always comprise at least SCM05, LR0029 and LK0036 and one or more of markers SCW09, CL922, SCV12, LR0096 and SCI11. The extended haplotypes are also predictive for the R-genes Dm3, Dm6 and R18 in coupling phase as found in seeds of the deposit which were deposited with the NCIMB under accession number NCIMB 41761 and may lead to a better identification of the presence of the genetic determinant.

The sequences of the markers are mentioned in Table 4, and the corresponding primers that may be used to amplify the markers are mentioned in Table 5.

One aspect of the invention thus relates to a genetic determinant which may comprise the R-genes Dm3, Dm6 and R18 in coupling phase, which may be identified in plants grown from seeds deposited under accession number NCIMB 41761 by a unique haplotype which may comprise at least marker SCM05 with SEQ ID NO:4, marker LR0029 with SEQ ID NO:5, and marker LK0036 with SEQ ID NO:6, and optionally also markers selected from the group consisting of marker SCW09 with SEQ ID NO:1, marker CL922 with SEQ ID NO:2, marker SCV12 with SEQ ID NO:3, marker LR0096 with SEQ ID NO:7, and marker SCI11 with SEQ ID NO:8.

In a still further embodiment the invention relates to a lettuce plant, which is resistant to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, and which plant is obtainable by crossing a lettuce plant grown from seeds of which a representative sample was deposited with the NCIMB under accession number NCIMB 41761, and selecting in the F2 progeny of the cross that is obtained after crossing the F1 with itself or with another plant for plants showing resistance to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28.

The invention further relates to a lettuce plant resistant to *Bremia lactucae* races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, wherein said resistance is conferred by resistance genes Dm3, Dm6 and R18, which genes are present in homozygous form, wherein said genes are obtainable by introgressing said genes from a plant grown from seeds of which a representative sample was deposited with the NCIMB under accession number NCIMB 41761, and wherein the said resistance genes are present in seed of deposit number NCIMB 41761 and are linked therein to marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

When the R-genes are not in coupling phase but in repulsion phase a similar resistance pattern may be found only in a plant which may comprise the R-genes in heterozygous state. This is for instance the case when a plant which may comprise the Dm3 resistance gene in homozygous state is crossed with a plant which may comprise Dm6 and R18 in homozygous state. A completely heterozygous F1 is obtained, which may comprise all R-genes, but on the different homologous chromosomes. When plants of such an F1 are selfed (FIG. 2), an F2 is obtained which consists for 50% out of plants fully resistant to all Bremia lactucae races covered by the R-genes Dm3, Dm6 and R18; 25% of the plants of the F2 only cover the resistances against the Bremia lactucae covered by Dm3 (see Table 1); and the remaining 25% of the plants are only resistant to those races covered by R-genes Dm6 and R18 (see Table 1). In case the F2 is tested with a mixture of three Bremia lactucae races unique for each R-gene (e.g. Bl:16, Bl:17, and Bl:18), 50% of the plants are scored as being resistant, while the others will all show symptoms of infection.

A plant of the invention which may comprise the R-genes Dm3, Dm6 and R18 in coupling phase would show a different result. When a plant which may comprise the R-genes Dm3, Dm6 and R18 in coupling phase in homozygous state is crossed with a fully susceptible plant, all F1 plants would be heterozygous and fully resistant to the Bremia lactucae races covered by all three R-genes. Selfing the F1, will lead to an F2 population consisting for 75% out of resistant plants and for 25% out of fully susceptible plants (FIG. 1), this in contrast with an F2 which may comprise the R-genes in repulsion phase as is described above and in FIG. 2. The R-genes Dm3, Dm6 and R18 when in coupling phase thus behave as a single dominant gene.

Distinguishing a plant which may comprise the R-genes in coupling phase in heterozygous form from a plant which may comprise the R-genes in coupling phase in homozygous form may be done by selfing the plant, resulting in an inbred offspring, for example selfing the F2-plant as shown in FIG. 1 into an F3-population, and selecting those plants from the F2 of which the entire inbred offspring is not susceptible to any of the Bremia races covered by R-genes Dm3, Dm6 and R18 as depicted in Table 1, or by selecting any plant from said inbred offspring of which all plants are resistant against the Bremia races covered by R-genes Dm3, Dm6 and R18 as depicted in Table 1.

In one aspect the invention thus relates to a lettuce plant resistant to Bremia lactucae race Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, wherein said resistance is conferred by resistance genes Dm3, Dm6 and R18, which genes are present in homozygous form, wherein said genes are obtainable by
a) crossing a susceptible plant with a plant grown from seeds of which a representative sample was deposited under NCIMB accession number 41761.
b) selfing the F1 progeny plants in order to obtain F2 progeny plants;
c) selecting F2 plants which are resistant to said Bremia lactucae races;
d) selfing each of the selected F2 plants in order to obtain an F3 progeny population;
e) selecting those plants in the F2 of which all F3 progeny plants are resistant to said Bremia lactucae races as plant having the said resistance in homozygous form, or selecting a plant from an F3 population not segregating for the said resistance;

Another aspect of the invention relates to a lettuce plant resistant to Bremia lactucae races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28, wherein said resistance is conferred by resistance genes Dm3, Dm6 and R18 which are present in coupling phase and said genes are present in heterozygous form, wherein said lettuce plant is obtainable from a cross between a susceptible lettuce plant with a plant grown from seeds of which a representative sample was deposited under NCIMB accession number 41761.

The seeds deposited under NCIMB 41761 comprise the R-genes Dm3, Dm6 and R18 in coupling phase, which are linked in the seeds of the seed deposit to marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

In the absence of molecular markers or in the event that recombination between the molecular markers and the genetic determinant have taken place and thus are not predictive anymore, equivalence of genetic determinants may still be determined by an allelism test. To perform an allelism test, material that is homozygous for the known determinant, a tester plant, is crossed with material that is homozygous for the genetic determinant that is to be tested. This latter plant is referred to as the donor plant. The donor plant to be tested should be or should be made homozygous for the genetic determinant to be tested. The skilled person knows how to obtain a plant that is homozygous for the genetic determinant to be tested. When in the F2 of the cross between a donor plant and a tester plant no segregation for the phenotype related to the genetic determinant is observed, the genetic determinants of the donor plant and the tester plant have been proven to be equivalent.

In one embodiment of the invention a lettuce plant is provided that may comprise the R-genes Dm3, Dm6 and R18 in coupling phase and thus, when crossed with a tester plant, that may comprise the said genes in coupling phase, representative seed of which as deposited with the NCIMB under accession numbers a NCIMB 41761, or a progeny plant thereof that may comprise the R-genes in coupling phase comprised in lettuce plants representative seed of which was deposited under accession number NCIMB 41761 or a plant derived therefrom and which may comprise the said R-genes in coupling phase, plants of first generation progeny (F1) of said cross show no segregation for the resistance against Bremia lactucae races Bl:1, Bl:4, Bl:5, Bl:6, Bl:7, Bl:10, Bl:12, Bl:13, Bl:14, Bl:15, Bl:16, Bl:17, Bl:18, Bl:21, Bl:22, Bl:23, Bl:24, Bl:25 and Bl:28.

In both the tester plant and the plant of the invention the genetic determinant which may comprise the three R-genes in coupling phase is present in homozygous condition. Plants of the second and further generations, if obtained by selfing also show no segregation for the said resistance pattern. The tester plant may be a plant of which representative seed was deposited with the NCIMB under accession number NCIMB 41761. When the genetic determinant responsible for the resistance against *Bremia lactucae* races B1:15, B1:16, B1:17, B1:18, B1:21, B1:22, B1:23, B1:24, B1:25 and B1:28 as comprised in the deposit is present in a plant, the plant is a plant of the invention.

In contrast with the other races of *Bremia lactucae* to which R-genes Dm3, Dm6 and R18 confer resistance, race B1:2 may show a very limited amount of sporulation in the seedling test. In practise, however, the plants of the invention are also resistant against B1:2 despite the fact that a limited amount of sporulation might occur in the seedling test.

Therefore, the invention also provides lettuce plants resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28 and also resistant to *Bremia lactucae* race B1:2, which resistances are conferred by the R-genes Dm3, Dm6 and R18 present in coupling phase on chromosome 2 in the plant of the invention.

Next to the resistances against the *Bremia* races B1:1, B1:4, B1:5, B1:6, B1:13, B1:15, and B1:17 (see Table 1), the Ra-gene closely linked to the Dm6 R-gene also confers resistance against root aphid (*Pemphigus bursarius*).

Thus, the invention also relates to lettuce plants resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28 and resistant to root aphid (*Pemphigus bursarius*), which resistances are conferred by the R-genes Dm3, Dm6, Ra and R18 present in coupling phase on chromosome 2 in the plant of the invention.

In a further aspect thereof the invention relates to lettuce plants resistant to *Bremia lactucae* races B1:1, B1:16, B1:17, B1:18, B1:21, B1:22, B1:23, B1:24, B1:25 and B1:28 and resistant to *Bremia lactucae* race B1:2 and to root aphid (*Pemphigus bursarius*), which resistances are conferred by the R-genes Dm3, Dm6, B1 and R18 present in coupling phase on chromosome 2 in the plant of the invention.

According to a further aspect thereof, the invention relates to propagation material capable of growing into a plant of the invention.

In one embodiment, such propagation material is formed by seed of a lettuce plant of the invention, wherein the plant that may be grown from the seed is resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

In another embodiment the propagation material capable of growing into a plant of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

In a further embodiment the invention relates to tissue culture of propagation material capable of growing into a plant of the invention.

Suitably, the plant produced from the propagation material shows the resistance to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, in particular the resistance as found in *Lactuca sativa* 10G.913566, representative seeds of which were deposited with the NCIMB under accession number NCIMB 41761.

The invention also relates to progeny of the plants, cells, tissues and seeds of the invention. Such progeny may in itself be plants, cells, tissues or seeds. As used herein the word "progeny" is intended to mean the first and all further descendants from a cross with a plant of the invention that may comprise the R-genes Dm3, Dm6 and R18 in coupling phase. "Progeny" also encompasses plants that carry the trait of the invention and are obtained from other plants or progeny of plants of the invention by vegetative propagation or multiplication.

In one embodiment the invention relates to progeny of a lettuce plant of the invention, wherein the progeny plant is resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

The invention further relates to the head of a lettuce plant of the invention.

The invention also relates to a food product, which may comprise the lettuce head or parts thereof, optionally in processed form. In particular, the food product may comprise leaves of the lettuce plant or parts thereof. The food product is for example a salad or a salad mixture which may comprise leaves of the lettuce plant of the invention.

Markers linked to the R-genes Dm3, Dm6 and R18 in coupling phase were developed on a population of F2 plants segregating for the trait of the invention, using publicly available markers which span a large part of the *Bremia* resistance cluster on chromosome 2. The markers listed in Table 4 formed a unique haplotype which is predictive for the presence of R-genes Dm3, Dm6 and R18 in coupling phase. Table 4 lists the sequences of the markers and Table 5 the corresponding primers used to amplify them.

The invention further relates to a nucleic acid molecule causative of resistance against *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28 which may comprise a DNA sequence which may comprise the three R-genes Dm3, Dm6 and R18 in coupling phase, which DNA sequence is positioned on chromosome 2 and linked to marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

The invention further relates to the use of said nucleic acid molecule and/or said markers linked to said nucleic acid molecule for the identification of plants which may comprise *Bremia lactucae* resistance conferring genes Dm3, Dm6 and R18 in coupling phase.

The invention also relates to the use of said nucleic acid molecule and/or said markers to develop other markers linked to the *Bremia lactucae* resistance conferring genes Dm3, Dm6 and R18 in coupling phase.

In one aspect, the invention relates to a process for producing lettuce plants which may comprise R-genes Dm3, Dm6 and R18 in coupling phase, which may comprise the step of selecting said lettuce plants from a population of lettuce plants segregating for these genes in coupling phase using marker SCW09 with SEQ ID NO:1, and marker CL922 with SEQ ID NO:2, and marker SCV12 with SEQ ID NO:3, and marker SCM05 with SEQ ID NO:4, and marker LR0029 with SEQ ID NO:5, and preferably also to marker LR0096 with SEQ ID NO:7, and marker SCI11 with SEQ ID NO:8.

The term 'genetic determinant' as used herein encompasses one or more QTLs, genes, or alleles. These terms are used interchangeably. 'Genetic background' or 'genetic information' may be used instead of 'genetic determinant', and may comprise more than one relevant QTL, gene, or allele. In addition, the phrase 'genetic determinants' may be used. 'Genetic background' may also include more of the genome than only the QTL, gene, or allele that is indicated or that is identified. Genetic background may in addition be defined as 'genotype'. A genetic determinant may be identified by the use of a molecular marker. A genetic determinant may alternatively be identified by the position on a genetic map, or by indication of the location on a linkage group or chromosome. When a genetic determinant is not linked to a specific molecular marker any longer, but its position on a chromosome as defined on a genetic map is unaltered, this genetic determinant is still the same as when it was linked to the molecular marker. The genetic trait that it confers is therefore also still the same. The 'genetic trait' is the trait or characteristic that is conferred by the genetic determinant. In this specific case where the R-genes Dm3, Dm6 and R18 are in coupling phase and behave as a dominant single gene also 'trait' and 'genetic determinant' may be used interchangeably. The genetic trait may be identified phenotypically, for example by performing a bioassay. However, also plant stages for which no phenotypic assay may be performed do carry the genetic information that leads to the genetic trait. 'Trait' or 'phenotypic trait' may be used instead of 'genetic trait'.

In one embodiment, the invention relates to lettuce plants of the invention that carry the genetic determinant which may comprise R-genes Dm3, Dm6 and R18 in coupling phase and having acquired said determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a noncrossable species or a synthetic gene.

The invention also relates to the germplasm of plants of the invention. The germplasm is constituted by all inherited characteristics of an organism and according to the invention encompasses at least the genetic determinant of the invention. The germplasm may be used in a breeding program for the development of *Bremia lactucae* resistant lettuce plants.

In one aspect the invention relates to a method for production of a lettuce plant which may comprise *Bremia* R-genes Dm3, Dm6 and R18 in coupling phase, which may comprise
a) crossing a plant which may comprise *Bremia* R-genes Dm3, Dm6 and R18 in coupling phase with another plant;
b) selfing the resulting F1 for obtaining F2 plants;
c) selecting plants which may comprise *Bremia* R-genes Dm3, Dm6 and R18 in coupling phase in the F2;
d) optionally performing one or more additional rounds of selfing or crossing, and subsequently selecting, for a plant which may comprise *Bremia* R-genes Dm3, Dm6 and R18 in coupling phase.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a lettuce plant which may comprise *Bremia* R-genes Dm3, Dm6 and R18 in coupling phase, which may comprise
a) crossing a plant which may comprise *Bremia* R-genes Dm3, Dm6 and R18 in coupling phase with another plant;
b) optionally backcrossing the resulting F1 with the preferred parent;
c) selecting for plants which may comprise *Bremia* R-genes Dm3, Dm6 and R18 in coupling phase in the F2 or BC1;
d) optionally performing one or more additional rounds of selfing or crossing or backcrossing, and subsequently selecting, for a plant which may comprise *Bremia* R-genes Dm3, Dm6 and R18 in coupling phase.

The invention additionally provides a method of introducing a desired trait into a lettuce plant which may comprise *Bremia* R-genes Dm3, Dm6 and R18 in coupling phase, which may comprise:
a) crossing a lettuce plant which may comprise *Bremia* R-genes Dm3, Dm6 and R18 in coupling phase, representative seed of which were deposited with the NCIMB under deposit number NCIMB 41761, with a second lettuce plant that may comprise a desired trait to produce F1 progeny;
b) selecting an F1 progeny that may comprise *Bremia* R-genes Dm3, Dm6 and R18 in coupling phase and the desired trait;
c) crossing the selected F1 progeny with either parent, to produce backcross progeny;
d) selecting backcross progeny which may comprise the desired trait and/or *Bremia* R-genes Dm3, Dm6 and R18 in coupling phase; and
e) optionally repeating steps c) and d) one or more times in succession to produce selected fourth or higher backcross progeny that may comprise the desired trait and *Bremia* R-genes Dm3, Dm6 and R18 in coupling phase. The invention includes a lettuce plant produced by this method.

In one embodiment selection for plants which may comprise *Bremia* R-genes Dm3, Dm6 and R18 in coupling phase is done in the F1 or in the backcross progeny. According to another aspect selection for the trait of the invention is started in the F2 of a cross or alternatively of a backcross.

In one embodiment, selection for plants which may comprise *Bremia* R-genes Dm3, Dm6 and R18 in coupling phase is started in the F3 or a later generation.

In a further embodiment the plant which may comprise the *Bremia* R-genes Dm3, Dm6 and R18 in coupling phase is a plant of an inbred line, a hybrid, a doubled haploid, or of a segregating population.

The invention further provides a method for the production of a lettuce plant which may comprise *Bremia* R-genes Dm3, Dm6 and R18 in coupling phase by using a doubled haploid generation technique to generate a doubled haploid line which may comprise the said *Bremia* R-genes Dm3, Dm6 and R18 in coupling phase.

The invention furthermore relates to hybrid seed and to a method for producing hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid lettuce plant which may comprise crossing a first parent lettuce plant with a second parent lettuce plant and harvesting the resultant hybrid lettuce seed, in which the first parent lettuce plant and/or the second parent lettuce plant may comprise *Bremia* R-genes Dm3, Dm6 and R18 in coupling phase.

The invention also relates to a method for the production of a lettuce plant which may comprise *Bremia* R-genes Dm3, Dm6 and R18 in coupling phase by using a seed that may comprise a genetic determinant in its genome that leads to *Bremia* R-genes Dm3, Dm6 and R18 in coupling phase for growing the said lettuce plant. The seeds are suitably seeds of which a representative sample was deposited with the NCIMB under deposit number NCIMB 41761.

The invention also relates to a method for seed production which may comprise growing lettuce plants from seeds of which a representative sample was deposited with the NCIMB under deposit number NCIMB 41761, allowing the plants to produce seeds, and harvesting those seeds. Production of the seeds is suitably done by crossing or selfing.

In one embodiment, the invention relates to a method for the production of a lettuce plant which may comprise *Bremia* R-genes Dm3, Dm6 and R18 in coupling phase by using tissue culture. The invention furthermore relates to a method for the production of a lettuce plant which may comprise *Bremia* R-genes Dm3, Dm6 and R18 in coupling phase by using vegetative reproduction.

In one embodiment, the invention relates to a method for the production of a lettuce plant which may comprise *Bremia* R-genes Dm3, Dm6 and R18 in coupling phase by using a method for genetic modification to introgress *Bremia* R-genes Dm3, Dm6 and R18 in coupling phase into the lettuce plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of lettuce plants that comprise *Bremia* R-genes Dm3, Dm6 and R18 in coupling phase wherein germplasm which may comprise *Bremia* R-genes Dm3, Dm6 and R18 in coupling phase is used. Representative seed of said plant which may comprise the genetic determinant and being representative for the germplasm was deposited with the NCIMB under deposit number NCIMB 41761.

In a further embodiment the invention relates to a method for the production of a lettuce plant which may comprise *Bremia* R-genes Dm3, Dm6 and R18 in coupling phase wherein progeny or propagation material of a plant which may comprise the genetic determinant conferring said *Bremia* R-genes Dm3, Dm6 and R18 in coupling phase is used as a source to introgress *Bremia* R-genes Dm3, Dm6 and R18 in coupling phase into another lettuce plant. Representative seed of said plant which may comprise the genetic determinant was deposited with the NCIMB under deposit number NCIMB 41761.

The invention provides preferably a lettuce plant showing *Bremia* R-genes Dm3, Dm6 and R18 in coupling phase, which plant is obtainable by any of the methods herein described.

The invention further relates to a cell of a lettuce plant (*Lactuca sativa*), which lettuce plant may comprise R-genes Dm3, Dm6, and R18 in coupling phase as present in a lettuce plant grown from seed of which a representative sample was deposited with NCIMB on 29 Sep. 2010 and having the accession number 41761.

The invention further relates to a cell of a lettuce plant (*Lactuca sativa*), which lettuce plant may comprise R-genes Dm3, Dm6, and R18 in coupling phase, which lettuce plant is obtainable by crossing a lettuce plant with a lettuce plant grown from seed of which a representative sample was deposited under NCIMB accession number 41761, and selecting for a lettuce plant that may comprise R-genes Dm3, Dm6, and R18 in coupling phase, and thus shows resistance to *Bremia lactucae* race B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

In one embodiment, the invention relates to the use of seeds, a representative sample of which has NCIMB accession number 41761, for transferring a genetic determinant that may comprise R-genes Dm3, Dm6, and R18 in coupling phase into another lettuce plant (*Lactuca sativa*).

In another embodiment, the invention relates to the use of a lettuce plant (*Lactuca sativa*) which lettuce plant may comprise R-genes Dm3, Dm6, and R18 in coupling phase as present in a lettuce plant grown from seed, of which a representative sample was deposited under NCIMB accession number 41761, as a crop.

The invention also relates to the use of a lettuce plant (*Lactuca sativa*) which may comprise R-genes Dm3, Dm6, and R18 in coupling phase as present in a lettuce plant grown from seed of which a representative sample was deposited under NCIMB accession number 41761, as a source of seed.

In yet another embodiment, the invention relates to the use of a lettuce plant (*Lactuca sativa*) which may comprise R-genes Dm3, Dm6, and R18 in coupling phase as present in a lettuce plant grown from seed of which a representative sample was deposited under NCIMB accession number 41761, as a source of propagating material.

Further, the invention relates to a lettuce plant (*Lactuca sativa*) which may comprise R-genes Dm3, Dm6, and R18 in coupling phase as present in a lettuce plant grown from seed of which a representative sample was deposited under NCIMB accession number 41761, for consumption.

In another embodiment, the invention relates to the use of the genetic determinant comprising R-genes Dm3, Dm6, and R18 in coupling phase, which is as present in seeds of which a representative sample was deposited under NCIMB accession number 41761, for conferring said genetic determinant to a lettuce plant (*Lactuca sativa*) not having R-genes Dm3, Dm6, and R18 in coupling phase.

In yet another embodiment, the invention relates to the use of a lettuce plant (*Lactuca sativa*) as a donor of R-genes Dm3, Dm6, and R18 in coupling phase as present in seeds of which a representative sample was deposited under NCIMB accession number 41761.

Table 4 lists the sequences of the markers linked to R-genes Dm3, Dm6 and R18. Table 5 lists the sequences of the primers, which are used to amplify the corresponding markers of Table 4.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Seedling Test

Seeds of seed lot 10G.913566 and seeds of a lettuce plant belonging to butterhead lettuce variety "Cobham Green" susceptible for *Bremia lactucae* races Bl:1 to Bl:28 were germinated on wetted filter paper in a closed container to establish an environment of relatively high humidity. After seedlings were established i.e. emergence of the cotyledons but the first leaf not yet visible, they were sprayed with a spore suspension of *Bremia lactucae* races Bl:16, Bl:17, and Bl:18. These races were chosen, because resistance against each of these races is covered by only one of the R-genes in coupling phase (see Table 1).

The inoculated seedlings were incubated under controlled conditions being 15° C. at 16 hours light, 8 hours dark regime. This seedling test follows more or less the protocol described by Bonnier et al. (New sources of major gene resistance in *Lactuca* to *Bremia lactucae*. Euphytica 61:3, 203-211 (1992)). After 8 days, infection was clearly established on the susceptible seedlings of the "Cobham Green" plants, while the seedlings grown from seed lot 10G.913566 showed no incidences of sporulation at all.

Example 2

A. Transfer of R-Genes in Coupling Phase and Phenotypic Identification by Seedling Test A plant grown from seed of seed lot 10G.913566 (deposited under accession number NCIMB 41761), which may comprise the *Bremia* R-genes Dm3, Dm6 and R18 in coupling phase but no other R-genes was crossed with a plant of butterhead lettuce variety "Cobham Green" susceptible for *Bremia lactucae* races Bl:1 to Bl:28, and thus containing no R-genes. F1 seeds were germinated and the resulting F1 plants were selfed in order to obtain F2 seeds.

Seedling tests as described in Example 1 were performed on twelve F2 seedlings resulting from each of the four selfed F1 plants (e.g. 48 F2 seedlings in total), as well as on four seedlings of each parent of the initial cross. On the four susceptible parent seedlings of "Cobham Green", and on approximately 25% (4/12, 3/12, 4/12, 2/12) of the F2 seedlings, sporulating oomycete mycelium on the surface of the cotyledon was observed. The remaining 35 F2 plants (approximately 75%) and all the resistant parent plants of seed lot 10G.913566 did not show any sporulating oomycete biomass and were considered to be resistant against Bl:16, Bl:17, and Bl:18, and thus which may comprise in their genome the R-genes Dm3, Dm6 and R18 in coupling phase.

This further demonstrates that the R-genes when in coupling phase, are inherited in a dominant monogenic fashion, since a Chi-square analysis of the observed segregation shows that there is no deviation in the F2 from the expected 3:1 segregation ratio (See also FIG. 1).

B. Transfer of R-Genes in Coupling Phase and Phenotypic Identification by Leaf Disc Test Another cross was made between a plant of variety "Cobham Green" and a plant of the invention (deposit accession number NCIMB 41761). Four F1 plants were selfed and from each F1 plant, twelve F2 seeds were germinated. In order to confirm the presence of the R-genes in coupling phase, leaf discs were taken from the individual F2 plants at the 10-leaf stage. Two leaf discs, per strain, per plant were incubated on wetted filter paper in a closed container to establish an environment of high relative humidity. These leaf discs were inoculated with spore suspensions of *Bremia lactucae* races Bl:16, Bl:17, or Bl:18. The inoculated leaf discs were incubated under controlled conditions of 15° C. at 16 hours light, 8 hours dark regime. This leaf disc test is based on the protocol described in Bonnier et al. (Euphytica, 61(3):203-211, 1992).

After 8, 11 and 14 days of incubation, the disease index was scored by manual inspection. The disease index is a measure for the level of infection and discriminates between the categories R (resistance) which means no obvious infection, RS (reduced susceptible) which means a significant reduction of the infection as compared to a susceptible control, and S (susceptible) which means heavily infected and strongly sporulating oomycete biomass.

For each fysio, 34 plants (71%) were found to be resistant, while 14 plants in each test were found to be susceptible for all three *Bremia* races (Table 2).

Furthermore, the results of the leaf disc test showed that the 34 resistant plants were resistant for all three *Bremia* races Bl:16, Bl:17, and Bl:18 (Table 2). Therefore, it may be concluded from the results that the R-genes in the deposit and the resistant offspring are present in coupling phase (see FIG. 1).

TABLE 2

Results from the leaf disc test as described in example 2b. For each plant of the four F2 populations their resistance (R) or susceptibilty (S) was scored

| | F2 pop. from plant 1 | | | F2 pop. from plant 2 | | | | F2 pop. from plant 3 | | | | F2 pop. from plant 3 | | | |
|---|---|---|---|---|---|---|---|---|---|---|---|---|---|---|---|---|
| Plant nr. | Bl. 16 | Bl. 17 | Bl. 18 | | Bl. 16 | Bl. 17 | Bl. 18 | | Bl. 16 | Bl. 17 | Bl. 18 | | Bl. 16 | Bl. 17 | Bl. 18 |
| 1.01 | R | R | R | 2.01 | R | R | R | 3.01 | R | R | R | 4.01 | S | S | S |
| 1.02 | R | R | R | 2.02 | S | S | S | 3.02 | R | R | R | 4.02 | S | S | S |
| 1.03 | R | R | R | 2.03 | R | R | R | 3.03 | R | R | R | 4.03 | R | R | R |
| 1.04 | R | R | R | 2.04 | R | R | R | 3.04 | S | S | S | 4.04 | S | S | S |
| 1.05 | R | R | R | 2.05 | R | R | R | 3.05 | R | R | R | 4.05 | R | R | R |
| 1.06 | R | R | R | 2.06 | S | S | S | 3.06 | S | S | S | 4.06 | R | R | R |
| 1.07 | S | S | S | 2.07 | R | R | R | 3.07 | R | R | R | 4.07 | R | R | R |
| 1.08 | S | S | S | 2.08 | R | R | R | 3.08 | R | R | R | 4.08 | R | R | R |
| 1.09 | R | R | R | 2.09 | R | R | R | 3.09 | S | S | S | 4.09 | R | R | R |
| 1.10 | R | R | R | 2.10 | R | R | R | 3.10 | R | R | R | 4.10 | R | R | R |
| 1.11 | R | R | R | 2.11 | R | R | R | 3.11 | R | R | R | 4.11 | R | R | R |
| 1.12 | S | S | S | 2.12 | S | S | S | 3.12 | S | S | S | 4.12 | S | S | S |

Example 3

Genotypic Identification of the R-Genes in Coupling Phase.

DNA was extracted and purified from the 48 F2 plants used in the leaf disc test, using standard available protocols.

PCR based markers SCW09, CL922, SCV12, SCM05, LR0029, LK0036, LR0096, and SCI11 (Table 4) were amplified using the corresponding primers mentioned in Table 5. For markers SCW09, SCV12, SCM05, and SCi11 the amplifications were performed using a standard Taq DNA polymerase enzyme. For the markers LR0029, LR0096, LK0036, and CL922 hot-start Taq with extra proof reading activity was used during the amplification (e.g. Plantinum® Taq polymerase, Invitrogen). The resulting PCR products were sequenced.

The sequence results correspond exactly with the leaf disc test results. 34 Plants exhibited the haplotype linked to Dm3, Dm6, and R18 in coupling phase, which means that for each of the resistant plants sequenced fragments corresponding to SEQ ID NO:1 to SEQ ID NO:8 were found (See Table 3). The 14 susceptible plants did not display this haplotype.

TABLE 3

Sequence data for the PCR based marker haplotype linked to the three R-genes in coupling phase for all F2 plants

| Plant nr. | Marker SCW09 | Marker CL922 | Marker SCV12 | Marker SCM05 | Marker LR0029 | Marker LK0036 | Marker LR0096 | Marker SCI11 |
|---|---|---|---|---|---|---|---|---|
| 1.01 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.02 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.03 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.04 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.05 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.06 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.07 | Not found | Not found | Not found | Not found | Not found | Not found | Not found | Not found |
| 1.08 | Not found | Not found | Not found | Not found | Not found | Not found | Not found | Not found |
| 1.09 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.10 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.11 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 1.12 | Not found | Not found | Not found | Not found | Not found | Not found | Not found | Not found |
| 2.01 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.02 | Not found | Not found | Not found | Not found | Not found | Not found | Not found | Not found |
| 2.03 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.04 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.05 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.06 | Not found | Not found | Not found | Not found | Not found | Not found | Not found | Not found |
| 2.07 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.08 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.09 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.10 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.11 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 2.12 | Not found | Not found | Not found | Not found | Not found | Not found | Not found | Not found |
| 3.01 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.02 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.03 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.04 | Not found | Not found | Not found | Not found | Not found | Not found | Not found | Not found |
| 3.05 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.06 | Not found | Not found | Not found | Not found | Not found | Not found | Not found | Not found |
| 3.07 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.08 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.09 | Not found | Not found | Not found | Not found | Not found | Not found | Not found | Not found |
| 3.10 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |

TABLE 3-continued

Sequence data for the PCR based marker haplotype linked to the three R-genes in coupling phase for all F2 plants

| Plant nr. | Marker SCW09 | Marker CL922 | Marker SCV12 | Marker SCM05 | Marker LR0029 | Marker LK0036 | Marker LR0096 | Marker SCI11 |
|---|---|---|---|---|---|---|---|---|
| 3.11 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 3.12 | Not found | Not found | Not found | Not found | Not found | Not found | Not found | Not found |
| 4.01 | Not found | Not found | Not found | Not found | Not found | Not found | Not found | Not found |
| 4.02 | Not found | Not found | Not found | Not found | Not found | Not found | Not found | Not found |
| 4.03 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.04 | Not found | Not found | Not found | Not found | Not found | Not found | Not found | Not found |
| 4.05 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.06 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.07 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.08 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.09 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.10 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.11 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| 4.12 | Not found | Not found | Not found | Not found | Not found | Not found | Not found | Not found |

TABLE 4

Markers linked to Dm3, Dm6 and R18 when in coupling phase

| Name | Sequence |
|---|---|
| SCW09 SEQ ID NO: 1 | AACAACGTAAATTTTCAAAAGAAAATTTTCATTTAAAATCATAT AAATCCTCATGACACATTTTATTAAAATCTCATTTGCTCAATTC ACAAAACATAACTCCATGTTTTAGTAATTAAAAATCCAGGATCC TCATAACTCTTTCTCTGGTGTGTACAATCAACCGGTGCCGTCCT GCGATCCTGAGAACCTGAAACACATAACACATAACACGGTAAGC ACGAAGCTTAGTGAGTTCCCCAAGATACCACATAAAATACATAT TAGCCACTCGAGGCTATAACTCTATGGACCATCTGGTCCTAACT CTGTGGACCCTCTGGTCCTAACTTTGTGGACCTTTCGGTCCTAA TTCTGTAAACTCTGGAACACAAACACAACATAAATCACATAGAA ATAATGCAGTGCATCACATCACATAAATAGCATACAAAATACTC TGTCACATAACTCTGATTACCACTCTAGGTAAAGTATAGTGAGA AGACTCACTTGGCAAGCTGAAAGCAGCTATCCTTACACTTGAAT CTTGAACTCGCCACCGCCTAACACATAGGATGAACATCTCTTAT AATAACACTTTTTCACGACTCAGATAATCGAAGGCGGCTCCTTC TCTTTCTAACTCTCTAAAGTGGGTAAAAGACCATTTTACCCTTC CAAGGCCTCTATTACTTATGTTGACCAAAACCCCAAAGTCAACA AAAGTCAAGCTCAAGTCAACAGTCCACATTTGACCCTACTCGTC GAGTGCACCCATGCGACTCGTCGAGTCCCCTCGCATCAATTGAA CTCTACCTAGGACTCACTCAGATTGTCGAGTTGACTCCCAACTC GGCGAGCCAACACTAGGTTAAGA |
| CL922 SEQ ID NO: 2 | GGCCTATTTCGGTAGTTCCTGCACCACCACAACCACAGTTCATT CAAGGTGGAGGTTCTGGAGCAAATGCAGGAGGGTAAATATTTGG TTAAGGTTAGTGCATGGGTTGTTAATTTTTGTTCTGGTAAATAA TGAAAAAAAATTAAAAAAAATTCAATAATTTGTTTTTGTAGGT GTCCATAGATTGCAACATGATTATGAGCAACATTAGTGCTACTT GAGTGGCAGGGCCTTTGATTTACCCTTGCAACCTATTCGCATT CTAGAGGTACCATTGCAACATGTTTCATGTAAACATTAACTTTT GTCTAATTTACATATTCGGTCCCTGTACTTAGCACCATTTGTTT CAAGATGTTAACTTTGTAAAACAAGGGGCAAATAGTCATTTCT AAGAATTTAAAAGCTTGAAACAGACTGTTAGGATCAAGACCAAA AGCATCATGGATAAAATAAATACCAAATTGTAAAATGGTTTTTT TTTTTGACTTAAAGAAAAAAATTACCTAAGCAAAAGGACCAACA TGTAATTTTGTCTAGTAAGGGTGAGTTCAAAACATAACCAAATT AGAGTAACTACTTTTAATTATTTGCGTTGTGTGGTTTTCTTAAT TATATAATTTAGAGTAACTACTTTTAACCTCATTCTAGTGCATA AATAAACCTGATGATACTTTTGTGATGCAGGTCATATACAATCA ATGCTCACCAGAGAAGTTATCTTCCGATTTGCTTCTAGTGACAG GAGAAGTGGCACCACTTGGCTT |

TABLE 4 -continued

Markers linked to Dm3, Dm6 and R18 when in coupling phase

| Name | Sequence |
|---|---|
| SCV12<br>SEQ ID NO: 3 | ACCCCCCACTACCATATCAATCTCAGGTGCATTTTCATCATCAT<br>CAAGCATGGAAAATGCAAGGCATAGCATAAATTCAACAACGATA<br>TCTTATCGTCTTCAACACATTATTCAGTGAGTTGAAATCCAAAA<br>TCATCATGTAAGATGCGACTAACATAAAACATACACCCGATAAA<br>TAGAAAAAAGGCAATGCTTACAACATATTGTCACAACCCAAAAC<br>CAGACAACATGTCTCCAAAAGAAATTATACTTTTTGGGTATCAG<br>ATAAGTGAAATCTTAAATTGAAGTGAAAAAGTTGCAGGACAAGT<br>GGGGGGT |
| SCM05<br>SEQ ID NO: 4 | GGGAACGTGTTAATTAGAGATGTATTGTGCTATAGGGGGACTAC<br>AGTTCGGCAGATCGGGTGATTAGCGATTTCAGGTTTACGATTTA<br>CCGAGACACACGAGGTGAGTCTTCTCACTATACTTTACCTTGAG<br>TAGGTAACCAGAGTTATGTGATAGAGTACTTGTATGCTATGTAT<br>GTCATGTGTTGTACTGCATTATTTCTATGTGATTTATGTGGTGC<br>ATGTTTATCAGAGCTAGAACCTGAGGGTTCACAGAGTTTGGGTG<br>CACGGACCCACAGAGTTATAGTCTAGAGTGGCTAATATGTGTTA<br>TATGTGGTATTTTGGGGAACTCACTAAGCCTTGTGCTTACAGTG<br>TTGATGTTATTGTTTCAGGTACTAGTGACGACCGCGGGAAGGCG<br>CCGGCTTGATCCATACACACACGTTCCC |
| LR0029<br>SEQ ID NO: 5 | GAGTGTGATGGTATTGAAGAAGTTGTTTCAAACAGAGATGATGA<br>GGATGAAGA |
| LK0036<br>SEQ ID NO: 6 | GCAAAGGCTGAAAAAGGTTGTGAAAGAAAAGAAAATGTTTAATT<br>TTATTGTTGAGGCGGTTGTAGGGGAAAAAACAGACCCCATTGCT<br>ATTCAATCAGCTGTGGCAGATTACCTAGGTATAGAGCTCAATGA<br>AAAAACTAAACCAGCAAGAACTGAGAAGCTTCGTAAATGGTTTG<br>TGGACAATTCTGCTGGTAAGAAGATCCTAGTCATACTCGACGAT<br>GTATGGCAGTTAGTTGACCTGA |
| LR0096<br>SEQ ID NO: 7 | AGACGATGTATGGCAACCAGTTGATTTGGAAGATATTGGTTTAA<br>GTCGTTTTCCAAATCAAGATGTTGACTTCAAGGTCTTGATTACA<br>TCACGGGACCAATCAGTTTGCACTGAGATGGGAGTTAAAGCTGA<br>TTTAGTTCTCAAGGTGAGTGTCCTGGAGGAAGTGGAAGCACACA<br>GTTTGTTCCTCCAATTTTTAGAACCTTCTGATGATGTCGATCCT<br>GAGCTCAATAAAATCGGAGAAGAAA |
| SCI11<br>SEQ ID NO: 8 | ACTCCTTGACGAGTTACACGGAGCAACTATTTTTTCTAAGATAG<br>ATCTCTGATCCGGCTACCACCAAATAAGAGTATCAGAAAAAGAC<br>GTTCATAAAACAGTGTTTCGCACATTCGACGACATTACGAGTTT<br>CTCGTCATGCCATTTGGCCTCACAAACGCACCATCCACTTTTCA<br>GTCCGCCATGAACGATCTCTTCAGACCCGCCCTTCAACGGTTCG<br>TGTTAGTCTTCTTGGATGACATCCTAGTCTTCAGTCCTTCCTTG<br>GATACTCATTATGAACACTTACGACTTGTTTTTCAAAGCTTACG<br>GGATCACCAATTTCACACCAAACCATCCAAATGTATGTTGCTA<br>TGCATGAGGTCTCTTTGCTGGGACACAAAATTTCATCAACTGGA<br>GTAGTACCAGAAGCAGACAATATACAAGTAATGTAACAATGCC<br>ACAACCCACATCCTTCACAACCTTTAGCGCTTACTTAGGATTGA<br>CGGGATATTACCGTCGATTTGTTCCCCTCTACGCCAAAATTGCA<br>GCACCTTTAACTAATATTCTTAAACTCAAATCTTTTGCGTGGAA<br>TAACTCAGCATAGGAGGCGTTTGAACAACTTAAGACAACCATGC<br>AAGACTTGGTGACGTTAGCCCTACCAGACTTCAACTCTCAATTT<br>GATGTAAACATAGATGCTTCAGGAATGGCAATTGGAGTACTGTT<br>ATCTCAAAACAACAGACCAATATCCTTTTTTATGTAACACCGGA<br>AATTTTCAAACAATTTTTCATTTAAAATCATATAATTCTCGT<br>AACACATTTCACAAAAATCTCACTGATTTAATTTACAAAACACA<br>ACTTCATAATTGTTTTGATTCATACTCCAGGATCCTCAAAACAT<br>AACTCTTGTTCTGGTGTGTACAATCAAGCCGGTGCCTTCCCGCG<br>ATCCTGAGAAAACCTGAAACACATATCACATAACACGGTAAGCA<br>CGAAGTTTAGTGAGTTCCCAAAATACCACATACAACAAATTAG<br>CCACTCGAGGCTATAACTCTGTAAGACCCTCCGGTCAATGTGTC<br>TCAGTCAGACCCTCCAGTCCCACAACTCTGATGGACCCTCTGGT<br>CCTAACTCTGTGACCC |

TABLE 5

Primers for use in detecting the markers of Table 4

| | |
|---|---|
| SCW09 forward primer SEQ ID NO: 9 | GTGACCGAGTGTAACAACGTAAAT |
| SWC09 reverse primer SEQ ID NO: 10 | GTGACCGAGTAGTCTTAACCTAGT |
| CL922 forward primer SEQ ID NO: 11 | ATGCGGGTCAACAACAATA |
| CL922 reverse primer SEQ ID NO: 12 | TGCCACTTCTCCTGTCACTA |
| SCV12 forward primer SEQ ID NO: 13 | ACCCCCCACTACCATATCAATCTC |
| SCV12 reverse primer SEQ ID NO: 14 | ACCCCCCACTTGTCCTGCAACTTT |
| SCM05 forward primer SEQ ID NO: 15 | GGGAACGTGTTAATTAGAGATGTA |
| SCM05 reverse primer SEQ ID NO: 16 | GGGAACGTGTGTGTATGGATCA |
| LR0029 forward primer SEQ ID NO: 17 | GGAAGTGCAGCAACTGGAAT |
| LR0029 reverse primer SEQ ID NO: 18 | AGGGAACAAAGTGGTGGTTG |
| LK0036 forward primer SEQ ID NO: 19 | GCAAAGGCTGAAAAAGGTTG |
| LK0036 reverse primer SEQ ID NO: 20 | TCAGGTCAACTAACTGCCATACA |
| LR0096 forward primer SEQ ID NO: 21 | AGACGATGTATGGCAACCAG |
| LR0096 reverse primer SEQ ID NO: 22 | TTTCTTCTCCGATTTTATTGAGC |
| SCI11 forward primer SEQ ID NO: 23 | ACATGCCGTGTATTACTCAGAGTT |
| SCI11 reverse primer SEQ ID NO: 24 | ACATGCCGTGACAGTATGAGACCG |

The invention is further described by the following numbered paragraphs:

1. A lettuce plant resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, which plant comprises a genetic determinant which causes the resistance and which genetic determinant is obtainable by introgression from a plant grown from seeds of which a representative sample was deposited under accession number NCIMB 41761, and wherein the said genetic determinant in the seeds of seed deposit number NCIMB 41761 is at least linked to marker SCM05 with SEQ ID NO:4, marker LR0029 with SEQ ID NO:5, and marker LK0036 with SEQ ID NO:6, and optionally also to one or more of the markers selected from the group consisting of marker SCW09 with SEQ ID NO:1, marker CL922 with SEQ ID NO:2, marker SCV12 with SEQ ID NO:3, marker LR0096 with SEQ ID NO:7, and marker SCI11 with SEQ ID NO:8.

2. A lettuce plant of paragraph 1, wherein the genetic determinant comprises genes Dm3, Dm6 and R18 in coupling phase.

3. A lettuce plant of paragraph 1 or 2, which plant is obtainable by crossing a lettuce plant grown from seeds of which a representative sample was deposited under accession number NCIMB 41761, and selecting in the F2 progeny of the cross that is obtained after crossing the F1 with itself or with another plant for plants showing resistance against *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

4. A lettuce plant of any one of the paragraphs 1-3, which is also resistant to *Bremia lactucae* race B1:2 and/or root aphid (*Pemphigus bursarius*).

5. Progeny of a lettuce plant of any one of the paragraphs 1-4, wherein the progeny plant is resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

6. Seed of a lettuce plant of any one of the paragraphs 1-5, wherein the plant that can be grown from the seed is resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

7. Propagation material capable of growing into a plant of any one of the paragraphs 1-5.

8. Propagation material of paragraph 7, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

9. Tissue culture of propagation material of paragraph 8 or 9.

10. Head of a lettuce plant of any one of the paragraphs 1-6.

11. Food product, comprising the lettuce head of paragraph 10, or leaves, or parts thereof, optionally in processed form.

12. A nucleic acid molecule which is causative of resistance against *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28 comprising a DNA sequence, which is positioned on chromosome 2 and linked to marker SCM05 with SEQ ID NO:4, marker LR0029 with SEQ ID NO:5 and marker LK0036 with SEQ ID NO:6, and preferably also to one or more of the markers selected from the group consisting of marker SCW09 with SEQ ID NO:1, and marker CL922 with SEQ ID NO:2, and marker SCV12 with SEQ ID NO:3, and marker LR0096 with SEQ ID NO:7, and marker SCI11 with SEQ ID NO:8.

13. Nucleic acid molecule of paragraph 12, which comprises the genes Dm3, Dm6 and R18.

14. Use of the markers as defined in paragraph 1, or use of the nucleic acid molecule of paragraph 12 or 13, to identify plants containing *Bremia lactucae* resistance conferring genes Dm3, Dm6 and R18 in coupling phase.

15. Use of the markers of paragraph 1, or use of the nucleic acid molecule of paragraph 13 or 14, to develop other markers linked to the *Bremia lactucae* resistance conferring genes Dm3, Dm6 and R18 in coupling phase.

16. A process for identifying lettuce plants comprising R-genes Dm3, Dm6 and R18 in coupling phase, comprising the step of selecting said lettuce plants from a population of lettuce plants segregating for these genes in coupling phase using marker SCM05 with SEQ ID NO:4, and marker LR0029 with SEQ ID NO:5, and marker LK0036 with SEQ ID NO:6, and optionally also to one or more of the markers selected from the group consisting of marker SCW09 with SEQ ID NO:1, and marker CL922 with SEQ ID NO:2, and marker SCV12 with SEQ ID NO:3, and marker LR0096 with SEQ ID NO:7, and marker SCI11 with SEQ ID NO:8.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce plant resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, wherein the lettuce plant comprises genes Dm3, Dm6 and R18 in coupling phase which causes the resistance, and which are present in a plant grown from seeds of which a representative sample was deposited under accession number NCIMB 41761, and wherein the genes Dm3, Dm6 and R18 in coupling phase are on chromosome 2 and comprising marker SCM05 with SEQ ID NO:4, marker LR0029 with SEQ ID NO:5, and marker LK0036 with SEQ ID NO:6.

2. The lettuce plant as claimed in claim 1, wherein the genes Dm3, Dm6 and R18 in coupling phase comprise one or more of the markers selected from the group consisting of marker SCW09 with SEQ ID NO:1, marker CL922 with SEQ ID NO:2, marker SCV12 with SEQ ID NO:3, marker LR0096 with SEQ ID NO:7, and marker SCI11 with SEQ ID NO:8.

3. The lettuce plant as claimed in claim 1, which plant is obtained by crossing a lettuce plant grown from seeds of which a representative sample was deposited under accession number NCIMB 41761, and selecting in the F2 progeny of the cross that is obtained after crossing the F, 1 with itself or with another plant for plants showing resistance against *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28.

4. The lettuce plant as claimed in claim 1, which is also resistant to *Bremia lactucae* race B1:2 and/or root aphid (*Pemphigus bursarius*).

5. A seed of the lettuce plant as claimed in claim 1, wherein the plant grown from the seed is resistant to *Bremia lactucae* races B1:1, B1:4, B1:5, B1:6, B1:7, B1:10, B1:12, B1:13, B1:14, B1:15, B1:16, B1:17, B1:18, B1:21, B1:22, B1:23, B1:24, B1:25 and B1:28, wherein the seed comprises genes Dm3, Dm6 and R18 in coupling phase which causes the resistance and comprises marker SCM05 with SEQ ID NO:4, marker LR0029 with SEQ ID NO:5, and marker LK0036 with SEQ ID NO:6, which are present in a plant grown from seeds of which a representative sample was deposited under accession number NCIMB 41761.

6. A propagation material comprising genes Dm3, Dm6 and R18 in coupling phase which causes the resistance, which are present in a plant grown from seeds of which a representative sample was deposited under accession number NCIMB 41761 capable of growing into a plant as claimed in claim 1.

7. The propagation material as claimed in claim 6, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast or cell.

8. A tissue culture of the propagation material as claimed in claim 6.

9. A head of the lettuce plant as claimed in claim 1.

10. A food product comprising the head of the lettuce plant of claim 9 or leaves of the head of the lettuce plant of claim 9.

* * * * *

SEQUENCE LISTING

```
<160> NUMBER OF SEQ ID NOS: 24

<210> SEQ ID NO 1
<211> LENGTH: 859
<212> TYPE: DNA
<213> ORGANISM: Lactuca sativa
<220> FEATURE:
<221> NAME/KEY: source
<222> LOCATION: 1..859
<223> OTHER INFORMATION: /mol_type="DNA"
      /organism="Lactuca sativa"

<400> SEQUENCE: 1
aacaacgtaa attttcaaaa gaaattttc atttaaaatc atataaatcc tcatgacaca      60
ttttattaaa atctcatttg ctcaattcac aaaacataac tccatgtttt agtaattaaa     120
aatccaggat cctcataact ctttctctgg tgtgtacaat caaccggtgc cgtcctgcga     180
tcctgagaac ctgaaacaca taacacataa cacggtaagc acgaagctta gtgagttccc     240
caagatacca cataaaatac atattagcca ctcgaggcta taactctatg gaccatctgg     300
tcctaactct gtggaccctc tggtcctaac tttgtggacc tttcggtcct aattctgtaa     360
actctggaac acaaacacaa cataaatcac atagaaataa tgcagtgcat cacatcacat     420
aaatagcata caaaatactc tgtcacataa ctctgattac cactctaggt aaagtatagt     480
gagaagactc acttggcaag ctgaaagcag ctatccttac acttgaatct tgaactcgcc     540
accgcctaac acataggatg aacatctctt ataataacac tttttcacga ctcagataat     600
cgaaggcggc tccttctctt tctaactctc taaagtgggg aaaagaccat tttacccttc     660
caaggcctct attacttatg ttgaccaaaa ccccaaagtc aacaaagtc aagctcaagt      720 caacagtcca catttgaccc tactcgtcga gtgcacccat gcgactcgtc gagtcccctc     780
gcatcaattg aactctacct aggactcact cagattgtcg agttgactcc caactcggcg     840
agccaacact aggttaaga                                                   859

<210> SEQ ID NO 2
<211> LENGTH: 770
<212> TYPE: DNA
<213> ORGANISM: Lactuca sativa
<220> FEATURE:
<221> NAME/KEY: source
<222> LOCATION: 1..770
<223> OTHER INFORMATION: /mol_type="DNA"
      /organism="Lactuca sativa"

<400> SEQUENCE: 2
ggcctatttc ggtagttcct gcaccaccac aaccacagtt cattcaaggt ggaggttctg      60
gagcaaatgc aggagggtaa atatttggtt aaggttagtg catgggttgt taattttgt      120 tctggtaaat aatgaaaaaa aaattaaaaa aaattcaata atttgttttt gtaggtgtcc     180
atagattgca acatgattat gagcaacatt agtgctactt gagtggcagg ggcctttgat     240 ttaccttgc aacctattcg cattctagag gtaccattgc aacatgtttc atgtaaacat      300
taacttttgt ctaatttaca tattcggtcc ctgtacttag caccatttgt ttcaagatgt     360
taacctttgt aaaacaaggg gcaaatagtc atttctaaga atttaaagc ttgaaacaga      420 ctgttaggat caagaccaaa agcatcatgg ataaaataaa taccaaattg taaatggtt      480
```

| tttttttttg acttaaagaa aaaaattacc taagcaaaag gaccaacatg taattttgtc | 540 |
| tagtaagggt gagttcaaaa cataaccaaa ttagagtaac tacttttaat tatttgcgtt | 600 |
| gtgtggtttt cttaattata taatttagag taactacttt taacctcatt ctagtgcata | 660 |
| aataaacctg atgatacttt tgtgatgcag gtcatataca atcaatgctc accagagaag | 720 |
| ttatcttccg atttgcttct agtgacagga gaagtggcac cacttggctt | 770 |

```
<210> SEQ ID NO 3
<211> LENGTH: 315
<212> TYPE: DNA
<213> ORGANISM: Lactuca sativa
<220> FEATURE:
<221> NAME/KEY: source
<222> LOCATION: 1..315
<223> OTHER INFORMATION: /mol_type="DNA"
      /organism="Lactuca sativa"

<400> SEQUENCE: 3
```

| acccccact accatatcaa tctcaggtgc attttcatca tcatcaagca tggaaaatgc | 60 |
| aaggcatagc ataaattcaa caacgatatc ttatcgtctt caacacatta ttcagtgagt | 120 |
| tgaaatccaa aatcatcatg taagatgcga ctaacataaa acatacaccc gataaataga | 180 |
| aaaaaggcaa tgcttacaac atattgtcac aacccaaaac cagacaacat gtctccaaaa | 240 |
| gaaattatac ttttgggta tcagataagt gaaatcttaa attgaagtga aaaagttgca | 300 |
| ggacaagtgg ggggt | 315 |

```
<210> SEQ ID NO 4
<211> LENGTH: 426
<212> TYPE: DNA
<213> ORGANISM: Lactuca sativa
<220> FEATURE:
<221> NAME/KEY: source
<222> LOCATION: 1..426
<223> OTHER INFORMATION: /mol_type="DNA"
      /organism="Lactuca sativa"

<400> SEQUENCE: 4
```

| gggaacgtgt taattagaga tgtattgtgc tataggggga ctacagttcg gcagatcggg | 60 |
| tgattagcga tttcaggttt acgatttacc gagacacacg aggtgagtct tctcactata | 120 |
| ctttaccttg agtaggtaac cagagttatg tgatagagta cttgtatgct atgtatgtca | 180 |
| tgtgttgtac tgcattattt ctatgtgatt tatgtggtgc atgtttatca gagctagaac | 240 |
| ctgagggttc acagagtttg ggtgcacgga cccacagagt tatagtctag agtggctaat | 300 |
| atgtgttata tgtggtattt tggggaactc actaagcctt gtgcttacag tgttgatgtt | 360 |
| attgtttcag gtactagtga cgaccgcggg aaggcgccgg cttgatccat acacacacac | 420 |
| gttccc | 426 |

```
<210> SEQ ID NO 5
<211> LENGTH: 53
<212> TYPE: DNA
<213> ORGANISM: Lactuca sativa
<220> FEATURE:
<221> NAME/KEY: source
<222> LOCATION: 1..53
<223> OTHER INFORMATION: /mol_type="DNA"
      /organism="Lactuca sativa"

<400> SEQUENCE: 5
```

| gagtgtgatg gtattgaaga agttgtttca aacagagatg atgaggatga aga | 53 |

<210> SEQ ID NO 6
<211> LENGTH: 242
<212> TYPE: DNA
<213> ORGANISM: Lactuca sativa
<220> FEATURE:
<221> NAME/KEY: source
<222> LOCATION: 1..242
<223> OTHER INFORMATION: /mol_type="DNA"
      /organism="Lactuca sativa"

<400> SEQUENCE: 6

```
gcaaaggctg aaaaaggttg tgaaagaaaa gaaaatgttt aattttattg ttgaggcggt     60 tgtagggggaa aaaacagacc ccattgctat tcaatcagct gtggcagatt acctaggtat   120
agagctcaat gaaaaaacta aaccagcaag aactgagaag cttcgtaaat ggtttgtgga   180
caattctgct ggtaagaaga tcctagtcat actcgacgat gtatggcagt tagttgacct   240
ga                                                                   242
```

<210> SEQ ID NO 7
<211> LENGTH: 245
<212> TYPE: DNA
<213> ORGANISM: Lactuca sativa
<220> FEATURE:
<221> NAME/KEY: source
<222> LOCATION: 1..245
<223> OTHER INFORMATION: /mol_type="DNA"
      /organism="Lactuca sativa"

<400> SEQUENCE: 7

```
agacgatgta tggcaaccag ttgatttgga agatattggt ttaagtcgtt ttccaaatca     60
agatgttgac ttcaaggtct tgattacatc acgggaccaa tcagtttgca ctgagatggg   120
agttaaagct gatttagttc tcaaggtgag tgtcctggag gaagtggaag cacacagttt   180
gttcctccaa ttttttagaac cttctgatga tgtcgatcct gagctcaata aaatcggaga   240
agaaa                                                                245
```

<210> SEQ ID NO 8
<211> LENGTH: 1116
<212> TYPE: DNA
<213> ORGANISM: Lactuca sativa
<220> FEATURE:
<221> NAME/KEY: source
<222> LOCATION: 1..1116
<223> OTHER INFORMATION: /mol_type="DNA"
      /organism="Lactuca sativa"

<400> SEQUENCE: 8

```
actccttgac gagttacacg gagcaactat ttttttctaag atagatctct gatccggcta     60
ccaccaaata agagtatcag aaaaagacgt tcataaaaca gtgtttcgca cattcgacga   120
cattacgagt ttctcgtcat gccatttggc ctcacaaacg caccatccac ttttcagtcc   180
gccatgaacg atctcttcag acccgccctt caacggttcg tgttagtctt cttggatgac   240
atcctagtct tcagtccttc cttggatact cattatgaac acttacgact tgttttttcaa   300 agcttacggg atcaccaatt tcacaccaaa ccatccaaat gtatgtttgc tatgcatgag   360
gtctctttgc tgggacacaa aatttcatca actggagtag taccagaagc agacaatata   420
caagtaatgt aacaatggcc acaacccaca tccttcacaa cctttagcgc ttacttagga   480
ttgacgggat attaccgtcg atttgttccc ctctacgcca aaattgcagc acctttaact   540
aatattctta aactcaaatc ttttgcgtgg aataactcag cataggaggc gtttgaacaa   600
```

```
cttaagacaa ccatgcaaga cttggtgacg ttagccctac cagacttcaa ctctcaattt    660
gatgtaaaca tagatgcttc aggaatggca attggagtac tgttatctca aaacaacaga    720
ccaatatcct tttttatgta acaccggaaa ttttcaaaca aatttttcat tttaaaatca    780
tataattctc gtaacacatt tcacaaaaat ctcactgatt taatttacaa aacacaactt    840
cataattgtt ttgattcata ctccaggatc ctcaaaacat aactcttgtt ctggtgtgta    900
caatcaagcc ggtgccttcc cgcgatcctg agaaaacctg aaacacatat cacataacac    960
ggtaagcacg aagtttagtg agttccccaa aataccacat acaacaaatt agccactcga   1020
ggctataact ctgtaagacc ctccggtcaa tgtgtctcag tcagaccctc cagtcccaca   1080
actctgatgg accctctggt cctaactctg tgaccc                             1116
```

```
<210> SEQ ID NO 9
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="forward primer"
      /organism="artificial sequences"

<400> SEQUENCE: 9
gtgaccgagt gtaacaacgt aaat                                            24

<210> SEQ ID NO 10
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="reverse primer"
      /organism="artificial sequences"

<400> SEQUENCE: 10
gtgaccgagt agtcttaacc tagt                                            24

<210> SEQ ID NO 11
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="forward primer"
      /organism="artificial sequences"

<400> SEQUENCE: 11
atgcgggtca acaacaata                                                  19

<210> SEQ ID NO 12
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="reverse primer"
      /organism="artificial sequences"
```

```
<400> SEQUENCE: 12
tgccacttct cctgtcacta                                           20

<210> SEQ ID NO 13
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="forward primer"
      /organism="artificial sequences"

<400> SEQUENCE: 13 acccccccact accatatcaa tctc                                     24

<210> SEQ ID NO 14
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="reverse primer"
      /organism="artificial sequences"

<400> SEQUENCE: 14 acccccccact tgtcctgcaa cttt                                     24

<210> SEQ ID NO 15
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="forward primer"
      /organism="artificial sequences"

<400> SEQUENCE: 15
gggaacgtgt taattagaga tgta                                      24

<210> SEQ ID NO 16
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="reverse primer"
      /organism="artificial sequences"

<400> SEQUENCE: 16
gggaacgtgt gtgtgtatgg atca                                      24

<210> SEQ ID NO 17
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="forward primer"
      /organism="artificial sequences"
```

<400> SEQUENCE: 17
ggaagtgcag caactggaat                                                      20

<210> SEQ ID NO 18
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="reverse primer"
      /organism="artificial sequences"

<400> SEQUENCE: 18
agggaacaaa gtggtggttg                                                      20

<210> SEQ ID NO 19
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="forward primer"
      /organism="artificial sequences"

<400> SEQUENCE: 19
gcaaaggctg aaaaaggttg                                                      20

<210> SEQ ID NO 20
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="reverse primer"
      /organism="artificial sequences"

<400> SEQUENCE: 20
tcaggtcaac taactgccat aca                                                  23

<210> SEQ ID NO 21
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="forward primer"
      /organism="artificial sequences"

<400> SEQUENCE: 21
agacgatgta tggcaaccag                                                      20

<210> SEQ ID NO 22
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="reverse primer"

```
        /organism="artificial sequences"

<400> SEQUENCE: 22
tttcttctcc gattttattg agc                                            23

<210> SEQ ID NO 23
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="forward primer"
      /organism="artificial sequences"

<400> SEQUENCE: 23
acatgccgtg tattactcag agtt                                           24

<210> SEQ ID NO 24
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="reverse primer"
      /organism="artificial sequences"

<400> SEQUENCE: 24
acatgccgtg acagtatgag accg                                           24
```